United States Patent
Carrez et al.

(10) Patent No.: US 8,967,150 B2
(45) Date of Patent: *Mar. 3, 2015

(54) OPERATING DRAPES WITH A WINDOW

(75) Inventors: Jean-Luc Carrez, Ecouen (FR); Valery Dalle, Gouvieux (FR); Xavier Hocq, Villers Pol (FR); Patrick Lestoquoy, Attiches (FR)

(73) Assignee: Vygon, Ecouen (FR)

( * ) Notice: Subject to any disclaimer, the term of this patent is extended or adjusted under 35 U.S.C. 154(b) by 1324 days.

This patent is subject to a terminal disclaimer.

(21) Appl. No.: 12/161,206

(22) PCT Filed: Jan. 19, 2007

(86) PCT No.: PCT/FR2007/000103
§ 371 (c)(1),
(2), (4) Date: Jun. 30, 2009

(87) PCT Pub. No.: WO2007/083032
PCT Pub. Date: Jul. 26, 2007

(65) Prior Publication Data
US 2009/0277460 A1 Nov. 12, 2009

(30) Foreign Application Priority Data
Jan. 19, 2006 (FR) ...................... 06 00482

(51) Int. Cl.
*A61B 19/08* (2006.01)

(52) U.S. Cl.
CPC ........... *A61B 19/08* (2013.01); *A61B 2019/085* (2013.01)
USPC ........................................................ 128/853

(58) Field of Classification Search
CPC ....................................................... A61B 19/08
USPC .................................. 128/849–853, 854–857
See application file for complete search history.

(56) References Cited

U.S. PATENT DOCUMENTS

| | | | |
|---|---|---|---|
| 2,521,550 A | 9/1950 | Smith | |
| 3,565,067 A * | 2/1971 | Bayer et al. | 128/853 |

(Continued)

FOREIGN PATENT DOCUMENTS

| | | |
|---|---|---|
| EP | 0494413 A | 7/1992 |
| EP | 0512876 A1 | 11/1992 |

(Continued)

*Primary Examiner* — Alireza Nia
*Assistant Examiner* — Tarla Patel
(74) *Attorney, Agent, or Firm* — Levine Mandelbaum PLLC

(57) ABSTRACT

The invention relates to an operating drape formed by an impermeable web that has a window (3) for access to the operating site, characterized in that the web consists of two impermeable sheets (10,20) held together, one along the extension of the other, in a sealed manner by an adhesive that allows the sheets to be separated by peeling and in that the window (3) is shared between the two sheets. The invention applies in particular to operating drapes used in surgery.

18 Claims, 4 Drawing Sheets

(56) References Cited

U.S. PATENT DOCUMENTS

| | | | |
|---|---|---|---|
| 3,680,135 A | 7/1972 | Boyer | |
| 3,930,497 A * | 1/1976 | Krebs et al. | 128/853 |
| 5,002,070 A | 3/1991 | Tayhlor et al. | |
| 5,127,423 A * | 7/1992 | Draeger | 128/849 |
| 5,345,946 A * | 9/1994 | Butterworth et al. | 128/853 |
| 5,515,868 A * | 5/1996 | Mills | 128/854 |
| 6,105,579 A * | 8/2000 | Levitt et al. | 128/849 |
| 6,129,085 A | 10/2000 | Jascomb | |
| 6,345,622 B1 | 2/2002 | Chandler et al. | |
| 6,966,320 B1 * | 11/2005 | Baynes | 128/853 |
| 7,086,404 B2 * | 8/2006 | Dusenbery et al. | 128/853 |
| 7,588,034 B2 * | 9/2009 | Mathis et al. | 128/849 |
| 2010/0186754 A1 * | 7/2010 | Carrez et al. | 128/853 |

FOREIGN PATENT DOCUMENTS

| | | |
|---|---|---|
| FR | 2841388 A1 | 12/2003 |
| GB | 2324244 A | 10/1998 |
| WO | 9904721 | 2/1999 |
| WO | 9916377 A | 4/1999 |

* cited by examiner

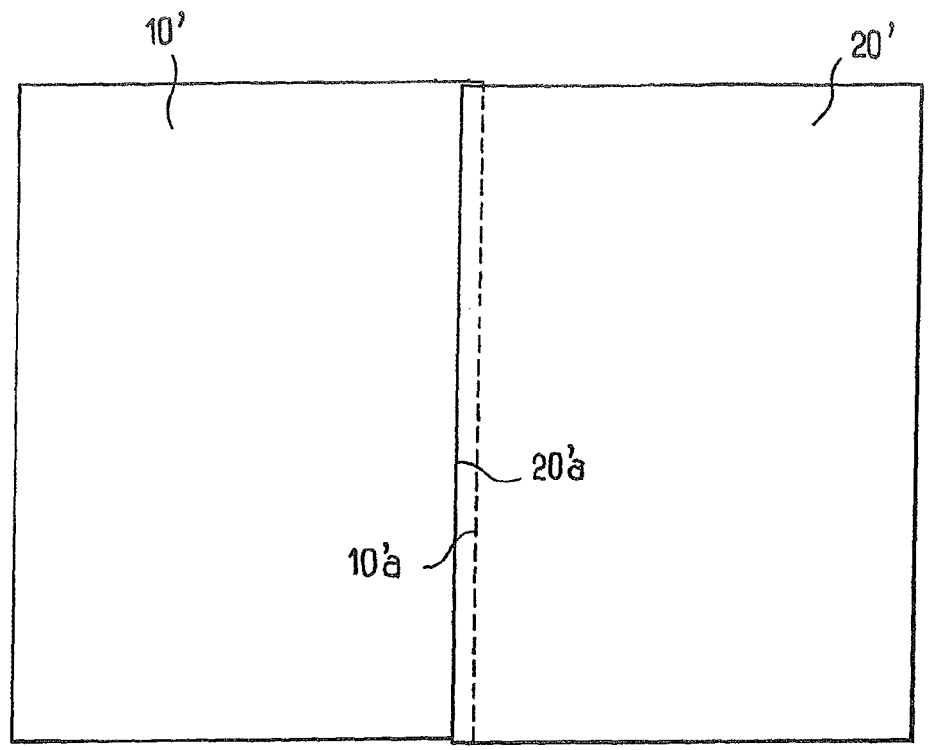
FIG_6
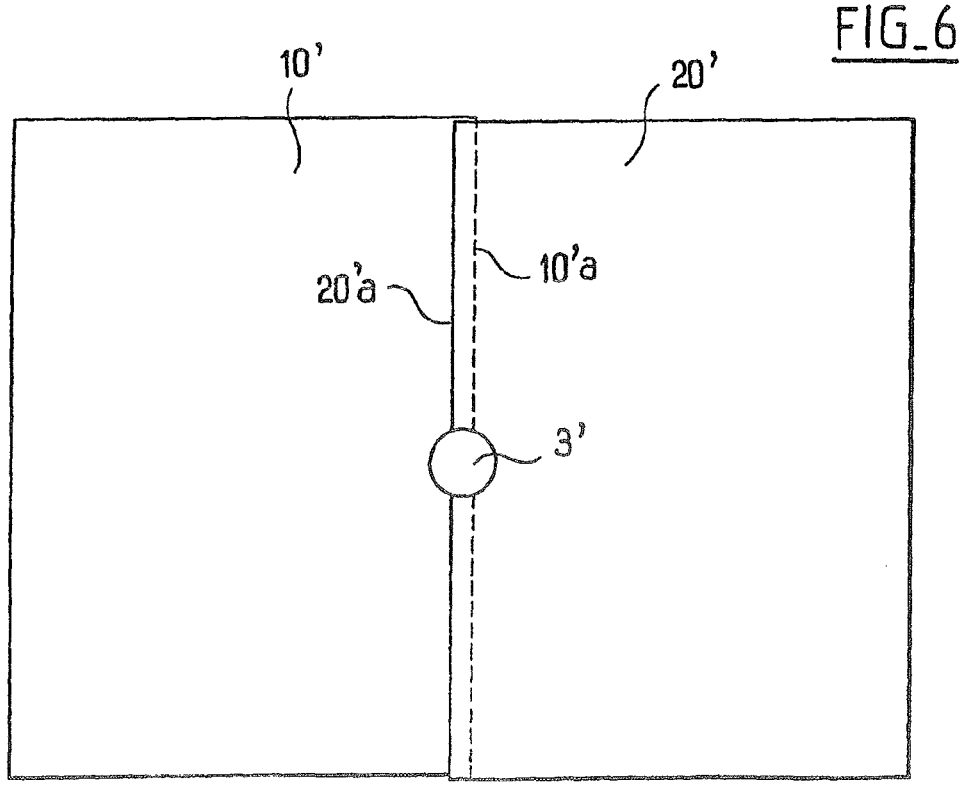
FIG_7

OPERATING DRAPES WITH A WINDOW

BACKGROUND OF THE INVENTION

The invention relates to an impermeable operating drape that includes a window through which the operating physician is able to access the operating site and to insert a tube or a wire into the body, possibly extended by a transfusion line or other line that must remain in position when the drape has to be removed.

In order to remove the drape despite the presence of the tube of the wire or of the line that is passing through the window, it is conventional to cut the drape by means of an instrument, or to tear the drape at the appropriate moment of its removal, until the window has been opened laterally, and these operations complicate the work of the operating physician, and constitute a risk for the tube, the wire or the line.

In order to facilitate these operations, it has been proposed that the drape should be equipped with tearing or cutting slits, as described in publication EP 1 009 318 for example.

These measures facilitate the division of the drape to a limited degree only, and do not eliminate the risks.

The present invention aims to enable easy and reliable removal of the drape without the use of a tool and without resorting to a tearable material for the constitution of the drape.

Publication WO 99/16377 described drapes with a window in which tear-lines are placed leading to the window and that are used to tear the drape in order to adapt it more easily to the shape of the face, and in particular of the eyebrows and eyelids, since it concerns a drape employed in ophthalmology.

The publication explains that these lines are composed of perforations or indentations or weakening of the sheet. In fact, the only method actually described is the cutting of perforations with a rotary cutter.

The problem of the present invention is to create a drape with a window for the operation, and to be able to separate it into two parts in order to remove it despite the tubes corning out from the operating site via the window and connected to appliances.

A drape with a pre-cut tear strip can allow this separation to occur, but it is not impermeable around the operating site. However it must be so because of questions of possible infections.

Indentations or a thermal weakening make the drape tearable, and favour the accidental formation of perforations.

The present invention is used to create impermeability without weakening the sheet, and to divide the sheet in two without the aid of a cutting tool.

SUMMARY OF THE INVENTION

According to the invention, this is achieved with an operating drape composed of an impermeable web that includes a window (3) providing access to the operating site, characterised in that the web is composed of two impermeable sheets (10, 20) arranged in extension of each other in a sealed manner by an adhesive that allows separation of the sheets by peeling them apart, and in that the window (3) is shared between the two sheets.

In preferred embodiments, the drape also has one or more of the following characteristics:
  the two sheets have two joined edges that are held by an impermeable ribbon placed under the said edges and to which the said edges are attached by the said adhesive;
  the two sheets have two edges superimposed, and the said adhesive is located between the said edges;
  the said edges are rectilinear;
    the said window is shared substantially equally between the two sheets;
  the said sheets are rectangular;
    absorbent means are provided around the window;
    the absorbent means are composed of two absorbent strips that are complementary, so as to form a frame around the window, and that are affixed to the drape except at positions where they overlap, so that they remain free at these positions;
    the drape includes several superimposed windows of decreasing size created in successive masks that are peelable laterally.

DESCRIPTION OF THE DRAWINGS

A description will now be provided of examples of the creation of an operating drape according to the invention/with reference to the attached figures, in which:

FIG. 6 represents the lower face of a variant of a drape according to the invention, before creation of the window, and FIG. 7 represents the drape of FIG. 6, after creating the window.

DESCRIPTION OF THE PREFERRED EMBODIMENT

Figure 1:
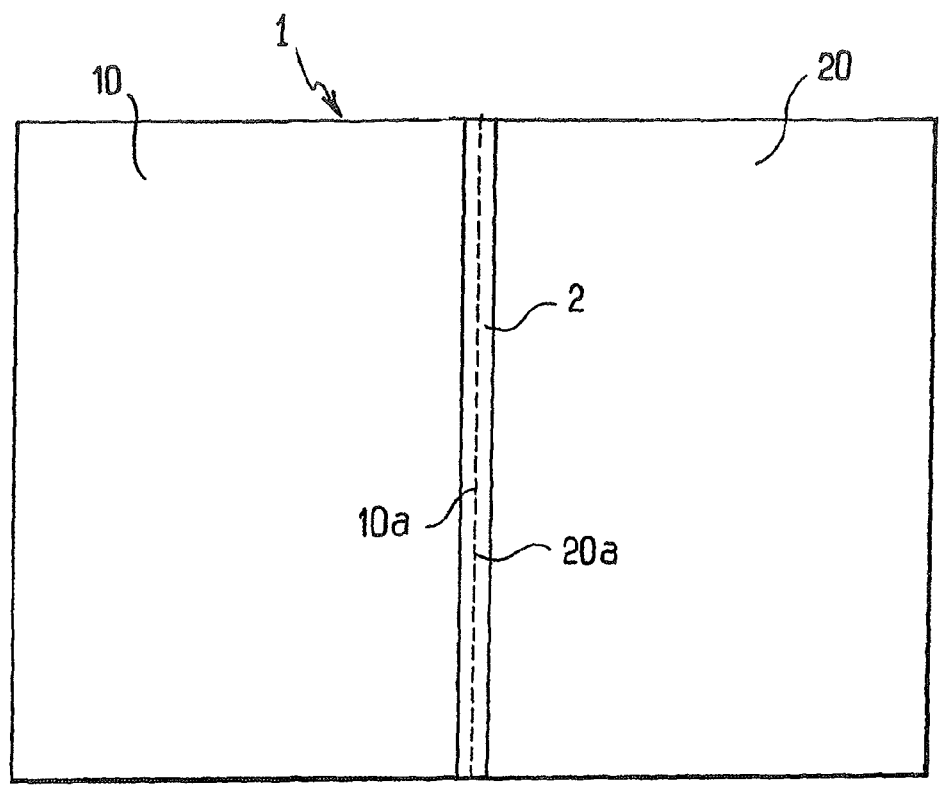
FIG. 1 represents the lower face of an embodiment of a drape according to the invention, meaning the face that will be in contact with the skin, before creation of the window.

The drape 1 represented in FIG. 1 is composed of two rectangular impermeable sheets 10, 20, measuring 100×70 cm for example, of which two edges 10a, 20a are joined. Under these edges, the sheets are attached by adhesive to an impermeable strip 2, measuring 5 to 10 cm wide for example, that allows the strip to be detached by peeling apart.

Figure 2:
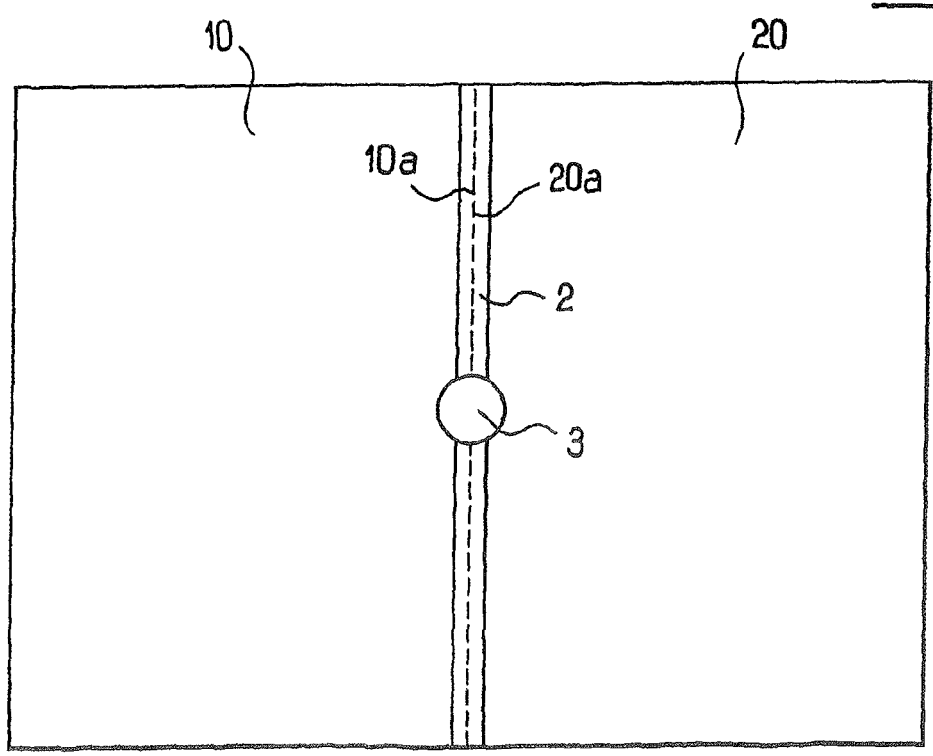
FIG. 2 represents the drape of FIG. 1 after the creation of a window.
Figure 3:
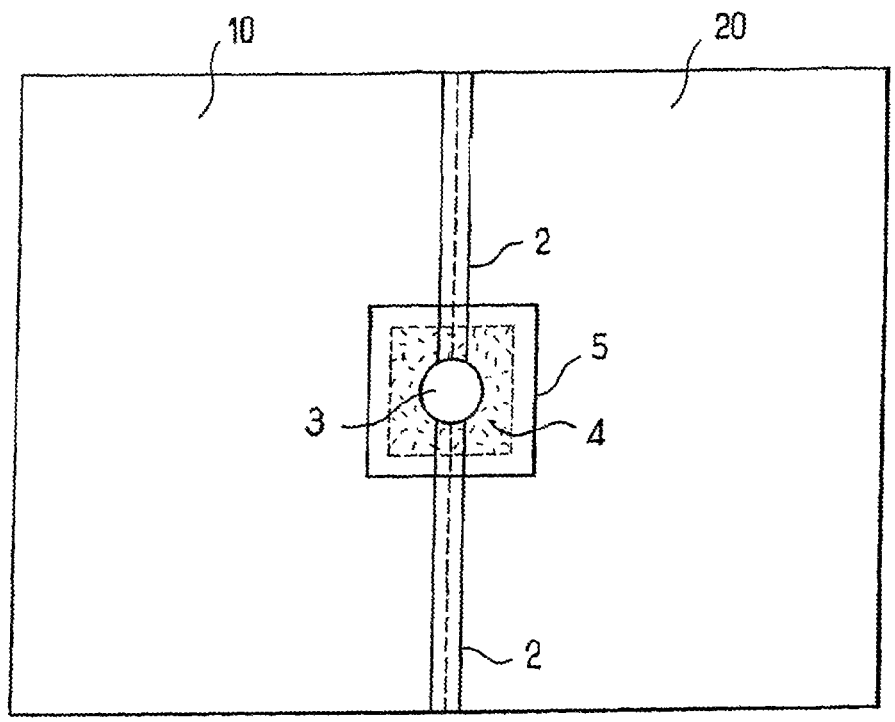
FIG. 3 represents the drape of FIG. 2 after the application of an adhesive.

A hole is created in the drape (FIG. 2), which constitutes a window 3 that is shared between the two sheets, substantially equally for example.

This window can have any shape and any dimensions desired, and can be circular (FIG. 2) or oval for example.

Adhesive 4 is applied around the hole on the lower face of the drape, and this adhesive, as well as the hole, is protected temporarily by a silicone paper 5 that will be removed for attachment of the drape around the operating site.

Figure 4:
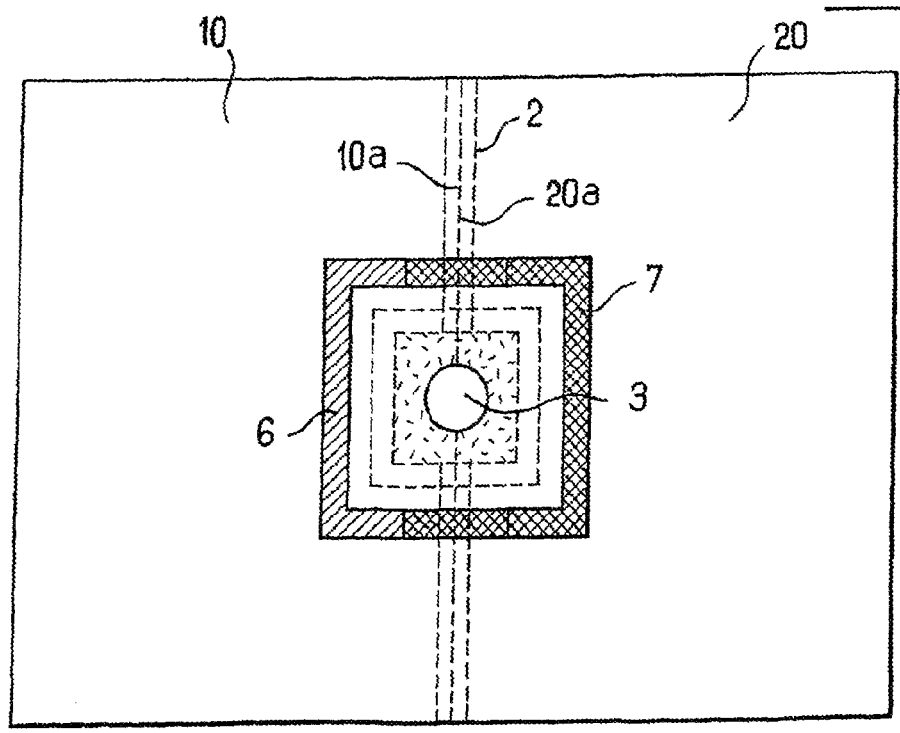
FIG. 4 represents the upper face of the drape after placement of the absorbent strips.

Two U-shaped strips 6, 7, in an absorbent material, in a non-woven material for example, are attached to the upper face of the drape (FIG. 4) by means of adhesive around the hole 3. The two strips are placed in opposition so that their wings overlap on the dividing line and are neither fixed at the positions of the overlap nor to the drape between them.

The U-shaped strips constitute an inside square of about 40 cm per side, and an outside square of 50 to 60 cm per side. On the inside of the 40 cm square, all the materials other than the silicone paper are preferably transparent.

In a manner that is familiar in its own right, the drape can include several superimposed windows whose size decreases from the initial window of the drape up to the topmost window.

Figure 5:
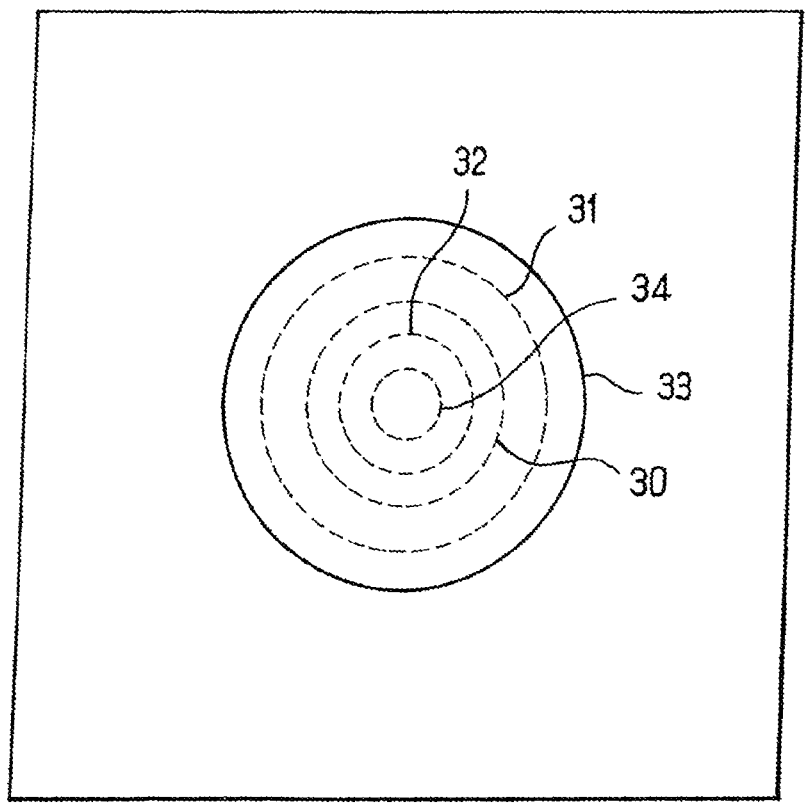
FIG. 5 represents the windows of a drape with several superimposed windows.

For example, FIG. 5 represents a drape that includes an initial window 30 that is 15 cm in diameter for example, covered by a first peelable adhesive mask 31 that itself includes a window 32, which 10 cm in diameter for example, and which is covered by a second peelable adhesive mask 33 fitted with a window 34 that is 5 cm in diameter for example. The masks are split in order to allow lateral peeling apart.

The silicone paper is removed when using the drape. The drape is applied to the skin of the patient. To this end, it is possible to see through the transparent square.

This is then followed by the operation and placement of the permanent lines (transfusion, blood-pressure measurement, and others), and then one of the sheets is separated from the adhesive base by peeling it laterally up to the hole at the operating site, the drape is then pulled laterally around the lines, and the U-shaped strips also separate around the installed lines without offering any resistance.

The drape is lifted from the skin of the patient before pulling it laterally.

The U-shaped strips serve to absorb liquids during the operation, and the square of non-woven material can be oriented so as to avoid having sides where the strips overlap in the lowered position of the drape.

In an alternative embodiment (FIGS. 6 and 7), the two sheets 10', 20' of the drape have two superimposed edges 10'a, 20'a; 10'a, 20'a and an adhesive that allows them to be peeled apart is placed between the superimposed edges. The adhesive can be applied in the form of a ribbon. The overlap of the two sheets can be 5 cm wide for example. The perforation 3' is created as before.

The invention is not limited to the embodiments that have just been described.

The invention claimed is:

1. An operating drape including an impermeable web having a window providing access to an operating site, said impermeable web comprising
   a first impermeable sheet having a surface with a margin coated with an adhesive,
   a second impermeable sheet in extension of said first impermeable sheet, and having a surface with a margin coated with said adhesive,
   an impermeable ribbon bonded to said margin of said first sheet and said margin of said second sheet, thereby maintaining said margin of said first sheet and said margin of said second sheet in mutual parallel juxtaposition, wherein first and second sheets arranged in extension of each other in a sealed manner by an adhesive that allows separation of the sheets by peeling them apart said adhesive being releasable for permitting said impermeable ribbon and at least one of said first sheet and said second sheet to be peeled apart for separation of said first sheet from said second sheet.

2. The operating drape according to claim 1, wherein said first sheet and said second sheet have respective edges which are held together when said impermeable ribbon is bonded by said adhesive to said first sheet and said second sheet.

3. The operating drape according to claim 2 wherein said edges are rectilinear.

4. The operating drape according to claim 1 wherein said window is shared substantially equally between said first sheet and said second sheet.

5. The operating drape according to claim 1, wherein said first sheet and said second sheet are rectangular.

6. The drape according to claim 1, comprising absorbent means around the window that are split for peeling apart laterally.

7. The drape according to claim 6, in which said absorbent means comprise two absorbent strips that are complementary so as to form a frame around said window, and overlap, said two strips being affixed to said drape except at positions where said two strips overlap, so that they remain free at these positions.

8. The drape according to claim 7, in which said absorbent strips are U-shaped.

9. The drape according to claim 1 comprising a plurality of superimposed windows of decreasing size created in successive peelable masks that are split for peeling apart laterally.

10. The drape according to claim 1 wherein said window permits passage therethrough of a tube or wire, and said window is partially within said first impermeable sheet and partially within said second impermeable sheet, said window being opened upon separation of said first sheet from said second sheet thereby permitting removal of said drape from said patient without disturbing said tube or wire.

11. The operating drape according to claim 10, wherein said first sheet and said second sheet have respective edges which are held together when said impermeable ribbon is bonded by said adhesive to said first sheet and said second sheet.

12. The operating drape according to claim 11 wherein said edges are rectilinear.

13. The operating drape according to claim 10 wherein said window is shared substantially equally between said first sheet and said second sheet.

14. The operating drape according to claim 10, wherein said first sheet and said second sheet are rectangular.

15. The drape according to claim 10, comprising absorbent means around the window that are split for peeling apart laterally.

16. The drape according to claim 15, in which said absorbent means comprise two absorbent strips that are complementary so as to form a frame around said window, and overlap, said two strips being affixed to said drape except at positions where said two strips overlap, so that they remain free at these positions.

17. The drape according to claim 16, in which said absorbent strips are U-shaped.

18. The drape according to claim 10 comprising a plurality of superimposed windows of decreasing size created in successive peelable masks that are split for peeling apart laterally.

* * * * *